(12) United States Patent
Hayden

(10) Patent No.: US 9,434,996 B1
(45) Date of Patent: Sep. 6, 2016

(54) ALL MINI-STR MULTIPLEX WITH INCREASED C.E. THROUGH-PUT BY STR PROLONGATION TEMPLATE FUSION

(71) Applicant: Tracy Ann Hayden, San Francisco, CA (US)

(72) Inventor: Tracy Ann Hayden, San Francisco, CA (US)

( * ) Notice: Subject to any disclaimer, the term of this patent is extended or adjusted under 35 U.S.C. 154(b) by 52 days.

(21) Appl. No.: 14/657,246

(22) Filed: Mar. 13, 2015

(51) Int. Cl.
*C12Q 1/68* (2006.01)

(52) U.S. Cl.
CPC ....... *C12Q 1/6888* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,427,930 A | 6/1995 | Birkenmeyer et al. | |
| 6,090,558 A * | 7/2000 | Butler | C12Q 1/6858 435/6.11 |
| 8,802,373 B2 | 8/2014 | Barany et al. | |

OTHER PUBLICATIONS

Zajac et al. (PLoS One, 2009, 4(11):e7823, p. 1-5).*
Lowe et al. (Nucleic Acids Research, 1990, 18(7):1757-1761).*
Butler, J.M. et al., "The Development of Reduced Size STR Amplicons as Tools for Analysis of Degraded DNA," Journal Forensic Science, vol. 48, Issue 5, Sep. 2003, 1054-1064.
Coble, M.D. and Butler, J.M., "Characterization of New MiniSTR Loci to Aid Analysis of Degraded DNA," Journal Forensic Science, vol. 50, Issue 1, Jan. 2005, 43-53.
Parsons, T.J. et al., "Application of novel 'mini-amplicon' STR multiplexes to high volume casework on degraded skeletal remains," Forensic Science International: Genetics, vol. 1, 2007, 175-179.
Kong, H et al., "Characterization of a DNA Polymerase from the Hyperthermophile Archaea Thermococcus litoralis," Journal of Biological Chemistry, vol. 268, Issue 3, 1993, 1965-1975.
Marshall, R.L. et al., "Detection of HCV RNA by the Asymmetric Gap Ligase Chain Reaction," Genome Research, vol. 4, 1994, 80-84.
Zajac, P. et al., "Analysis of Short Tandem Repeats by Parallel DNA Threading," PLOS One, vol. 4, Issue 11, Nov. 2009, e7823.
Wiedmann, M. et al., "Ligase chain reaction (LCR)—overview and applications," Genome Research, vol. 3, 1994, S51-S64.

* cited by examiner

*Primary Examiner* — Stephanie K Mummert

(57) ABSTRACT

A longstanding challenge in forensics is maximizing the number of "mini"—short tandem repeat amplicons within the limited confines of fluorescent channels and run length afforded by capillary electrophoresis. The instant disclosure overcomes this longstanding challenge by fusing mini-STR amplicons in a locus specific manner with a DNA construct of defined length. Staggering the lengths of the DNA constructs allows for staggering the mini-STRs in a locus specific manner. Beyond maximizing mini-STRs, the disclosed methods, compositions and kits can dramatically increase throughput of forensic samples by capillary electrophoresis.

7 Claims, 2 Drawing Sheets

ALL MINI-STR MULTIPLEX WITH INCREASED C.E. THROUGH-PUT BY STR PROLONGATION TEMPLATE FUSION

RELATED APPLICATIONS

None

BACKGROUND

Short tandem repeat (STR) DNA sequences are interspersed throughout the human genome at up to several hundred thousand loci. These loci are highly polymorphic with respect to the number of repeat units they contain and may vary in internal structure as well. Variation in the number of STR repeat units at a particular locus causes the length of the DNA at that locus to vary from allele to allele.

While the alleles at a single STR locus may be the same for two different individuals in a population, especially if the individuals are genetically related, the probability that the alleles of two individuals will be identical at several different loci becomes smaller and smaller as the number of loci examined increases. By determining the alleles at a sufficiently large number of loci in two different DNA samples it is possible to establish with virtual certainty whether or not the two samples originally came from the same individual.

Characterization of the alleles at specific STR loci for purposes of individual identification usually begins with the PCR amplification of genomic DNA. A primer pair that hybridizes to unique DNA sequences that flank the repeat region are used to amplify the STR locus. By using multiple primer pairs, it is possible to amplify multiple STR loci in the same reaction; a technique referred to as multiplexing. The resulting PCR products can be separated by electrophoresis and identified by comparison to known DNA standards.

Though techniques for analyzing STR loci, especially using capillary electrophoresis (CE) and fluorescent detection have been known and utilized for 20 years or so, there remains a need for new methods and compositions for analyzing STR loci. Disclosed herein are methods, compositions and kits for expanding the functionality of CE generally and for forensic analysis in particular.

BRIEF SUMMARY

Degraded DNA samples are commonly observed in forensic investigations involving biological evidence. When DNA is degraded STR profiles can be difficult to obtain using conventional STR typing. It has been reasoned that the farther removed a primer is from the STR locus the more likely a break will occur between the primer and the locus. Supporting this reasoning, recovery of amplified STR loci from degraded samples is often enhanced by use of smaller PCR products; that is reducing the distance between the primers and the STR locus. These so-called "mini-STR" assays (hypertext transfer protocol://www.cstl.nist.gov/strbase/miniSTR.htm) can help recover information from degraded DNA samples.

Typically, STR amplification products are resolved by mobility separation using capillary electrophoresis (CE) and detection by fluorescent dyes. A constraint on resolving mini STRs using CE and fluorescent dyes inherently exists though. Mobility separation requires amplification products possess different mobilities and this is related to the product size. To overcome this constraint, STR assays have been introduced with increasing numbers of fluorescent labels. Thus, each amplicon can be small being, differentiated by a different fluorescent label. But, the number of fluorescent labels is limited.

The instant disclosure provides a wholly different approach. The method disclosed entails in some embodiments combining a sample, a first primer, a second primer and a prolongation template along with amplification and ligation reactants to form a reaction mixture. The reaction mixture is then subjected to a contemporaneous amplification and ligation reaction after which the mixture is subjected to a separation process and thereby distinguishing the amplified target sequence, if any, wherein the target sequence is a short tandem repeat. In some embodiments the prolongation template is the reverse complement of a sequence flanking the target sequence over its entire length. In other embodiments the prolongation template encompasses a sequence that is the reverse complement of a sequence flanking the target sequence (the complementary prolongation template region), and a sequence that is not complementary to a sequence flanking the target sequence (the non-complementary prolongation template region). In some embodiments the non-complementary prolongation template region sequence is longer in nucleotides than a primer that is its reverse complement.

In some embodiments, a composition is disclosed encompassing an allelic ladder. An allelic ladder contains a set of alleles that are representative of those found in a particular STR locus. Allelic ladders provide a reference size marker for each allele included in the ladder and as such are often generated with the same primers as those used to amplify the target. In some embodiments, the allelic ladder encompassing more than one allele of an STR locus in combination with a prolongation template, wherein the prolongation template encompasses a sequence that is the reverse complement of a sequence flanking the target STR locus and a sequence that is not the reverse complement of a sequence flanking the target STR locus.

In some embodiments a kit of components is disclosed, the kit encompassing a first primer, a second primer and a prolongation template, wherein the first primer and the prolongation template possess sequence that is the reverse complement of sequence flanking an STR locus and the second primer is the reverse complement of sequence present in the prolongation template. In other embodiments, the kit also encompasses a container with a polymerase, a container with a ligase, a container with a first primer, a second primer and a prolongation template and a container with a buffer, wherein the first primer and the prolongation template possess sequence that is the reverse complement of sequence flanking an STR locus and the second primer is the reverse complement of sequence present in the prolongation template. While in other embodiments, the kit encompasses a container with an allelic ladder, a polymerase, a container with a ligase, a container with a first primer, a second primer and a prolongation template and a container with a buffer. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than the second primer that is its reverse complement.

DETAILED DESCRIPTION

Figure 1A:
FIG. 1 is an overview of the disclosed scheme. (A) Primer 1, Primer 2, the Prolongation Template and genomic DNA are present in a reaction mixture. Primer 1 and the Prolongation template, in this instance, are both the reverse complement to a genomic DNA sequence flanking a short tandem repeat (STR) locus. Primer 2 is the reverse complement to Prolongation Template sequence. (B) Upon melting of the genomic DNA, Primer 1 and the Prolongation Template hybridize through complementary base pairing to sequences flanking the target sequence, in this instance a short tandem repeat locus. (C) Target dependent extension of Primer 1 through the STR sequence reaches the 5' end of the Prolongation Template. The extended primer sequence and the prolongation template are then joined. (D) Primer 2 hybridizes to its reverse complement on the Prolongation Template and undergoes target dependent extension. In this instance the Prolongation Template possess a reverse complementary Prolongation Template region that is the reverse complement of a region flanking the target sequence and a sequence that is non-complementary to a region flanking the target sequence. (E) A product molecule.
Figure 1B:
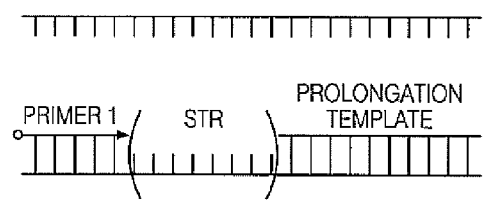
Figure 1C:
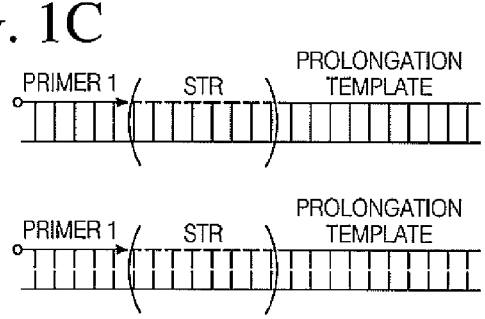
Figure 1D:
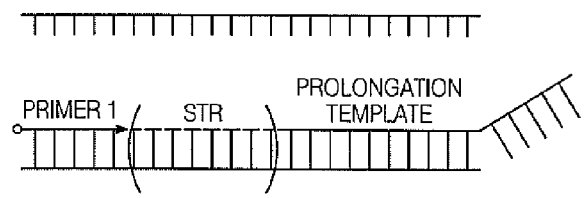
Figure 1E:
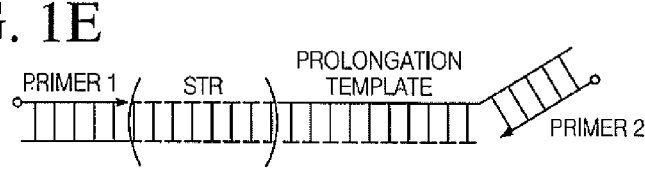
Figure 2:
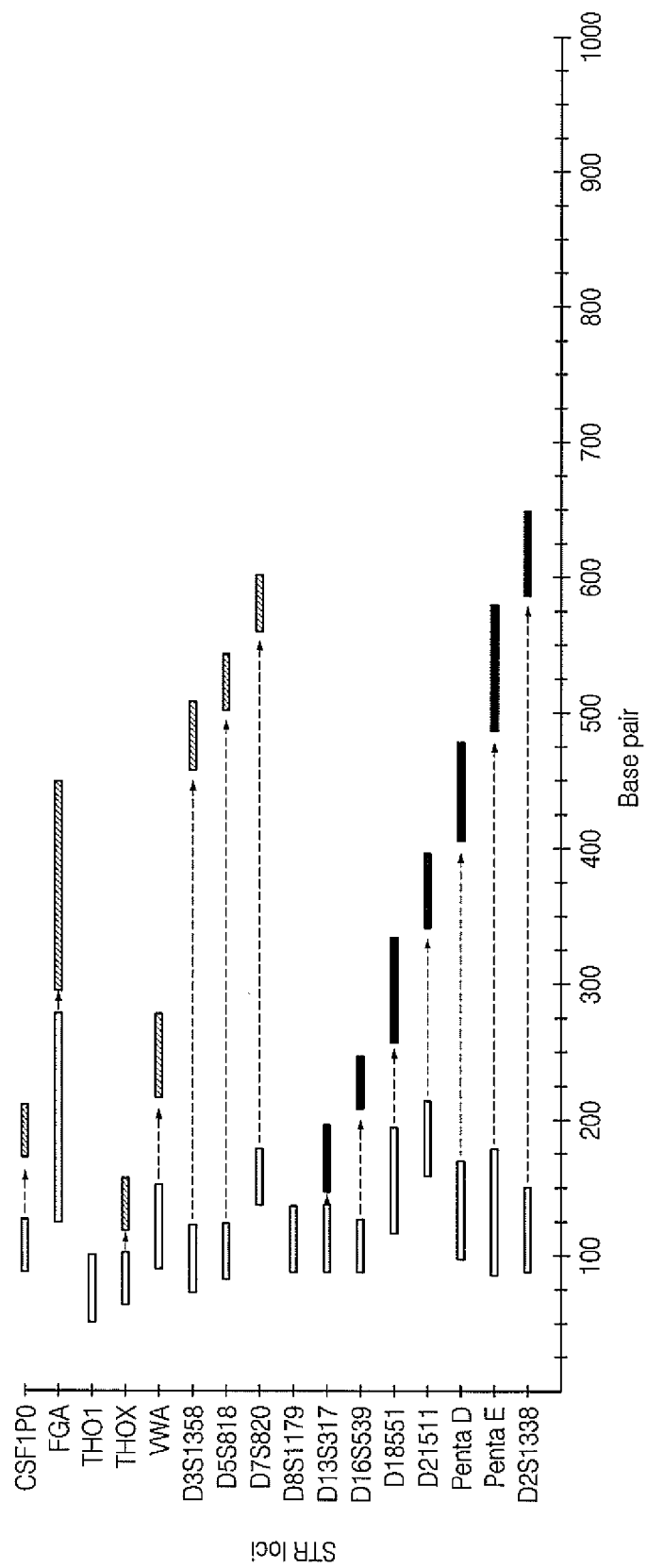
FIG. 2 depicts a representation of size range of STR alleles for the indicated loci when amplified without a Prolongation Template using primer pairs such as those described by Butler et al. in "The Development of Reduced Size STR Amplicons as Tools for Analysis of Degraded DNA" (2003) with the size range depicted as solid lines and the primer sequences and the partial Prolongation Template sequences of Table 1. Boxes depict a representation of the same loci when amplified in the presence of a Prolongation Template. In this way the amplified STR are "mini-STRs," with the addition of the prolongation template allowing for the manipulation of the mobility of the amplified STRs such that they can each be resolved by capillary electrophoresis.

Since the tragedy of the Branch Davidian fire in 1995, it has been recognized that smaller sized PCR products from short tandem repeat (STR) loci produce a higher success rate with degraded DNA samples. To generate these smaller sized PCR products, the PCR primers are made such they are as close as possible to the STR repeat region. The resulting PCR products are then resolved by mobility, which is related to size.

PCR products can be rendered distinguishable by using different fluorescent labels or by designing primers so that the resulting PCR products do no overlap in size. Often these two approaches can be used in concert. But, the flexibility of primer location is lost when the goal is to minimize the size of the PCR product. In such an instance, resolving PCR products becomes largely dependent on using differential labels, which are limited in number.

To generate smaller sized PCR products while working within the confines of a limited number of labels the instant disclosure provides a method. This method entails in some embodiments combining a sample, a first primer, a second primer and a prolongation template along with amplification and ligation reactants to form a reaction mixture. The reaction mixture is then subjected to a contemporaneous amplification and ligation reaction after which the reaction mixture is subjected to a separation process and thereby distinguishing the amplified target sequence, when present. This method affords the minimizing of the length of an amplified target sequence, the target sequence being a short tandem repeat, while increasing the capacity to distinguish between amplified short tandem repeat loci. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement.

A "short tandem repeat" (STR) is a genomic locus that contains repetitive sequence elements of from 2 to 7 nucleotides. Each sequence element, a repeat unit, is repeated at least once within an STR. Examples of STR sequences would be: ATCATCATCATCATCATC (SEQ ID NO:1) with the repeat unit "ATC;" GATAGATAGATACATAGATA (SEQ ID NO:2) with the repeat unit "GATA;" and ATTGCATTGCATTGC (SEQ ID NO:3) with the repeat unit "ATTGC" and so on.

In certain instances the repeat unit is repeated in tandem, as shown above. In other instances the repeat unit can be separated by intervening bases or deletions provided that at least in one instance the repeat unit is repeated in tandem once. These are referred to as "imperfect repeat," "incomplete repeat," and "variant repeat." Examples of this would be the imperfect repeat ATCGATCGAACGATCGATCG (SEQ ID NO. 4), the incomplete repeat AATGAATGAATGATG (SEQ ID NO. 5) and the variant repeat ATCCATCGATCCATCG ATCGATCCATCC (SEQ ID NO:5).

STR loci are preferred for determining identity because of the powerful statistical analysis that is possible with these markers. Individuals can possess different numbers of repeat units and sequence variations at a STR locus. These differences are referred to as "alleles." Each STR locus often has multiple alleles. As the number of STR loci analyzed increases the probability that any two individuals will possess the same set of alleles becomes vanishingly small.

STR alleles are typically categorized by the number of repeat units they contain. For example, an allele designated 12 for a particular STR locus would have 12 repeat units. Incomplete repeat units are designated with a decimal point following the whole number, for example, 12.2.

It is estimated that over 100,000 STR loci exist in the human genome. Among this large number of STR loci, the U.S. forensics community has established a set of 13 human STR loci that can be used to develop a genetic profile for the identification of individuals. This set of 13 loci, often referred to as the "CODIS loci," includes the following STR loci: CSF1PO, FGA, TH01, TPDX, vWA, D3S1358, D5S818, D7S820, D8S1179, D13S317, D16S539, D18S51 and D21S11. Beyond the CODIS loci, other STR loci are routinely used for human identification purposes. These additional loci include D2S1338, D19S433, D12S391, D1S1656, D2S441, MOS1248, D22S1045, SE33, Penta D, Penta E and D6S1043. Information about these loci, such as the number of alleles and sequences, can be found, among other sources, at the STRbase on the world wide web. cstl.nist.gov/strbase.

Accordingly in some embodiments, a method is disclosed that entails combining a sample, a first primer, a second primer and a prolongation template along with amplification and ligation reactants to form a reaction mixture. The reaction mixture is then subjected to a contemporaneous amplification and ligation reaction after which the reaction mixture is subjected to a separation process and thereby distinguishing an amplified target sequence, when present, wherein the target sequence is anyone of the STR loci CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement.

The methods disclosed utilize a sample. "Sample" refers to a solid or liquid suspected of containing a nucleic acid. The sample can be a filter paper upon which cells have been collected; for instance, buccal cells, blood cells, semen or vaginal fluids. The sample can be a filter paper having been contacted to a surface, for instance a surface on which there is a fingerprint. The sample can be cloth upon which cells have been deposited. For instance, the sample can be cloth upon which blood, saliva, semen or vaginal fluids have been applied. The sample can be a swab, or a portion thereof, upon which cells have collected; for instance, buccal cells, blood cells, semen or vaginal fluids. The swab can be made of materials such as cotton or Nylon®. The sample can be a swab having been contacted to a surface; for instance a surface on which there is a fingerprint, blood, saliva or vaginal fluids.

In other instances, the sample can be an extract of a biological specimen. A "biological specimen" can be a eukaryote cell, a prokaryote cell or a virus. Examples of a biological specimen are whole blood, plasma, serum, saliva, sweat, vaginal secretions, semen, tissues, urine or cerebrospinal fluid. The extract of a biological sample can include a nucleic acid. The nucleic acid can be DNA.

Accordingly, in some embodiments a method is disclosed that entails combining DNA, a first primer, a second primer and a prolongation template along with amplification and ligation reactants to form a reaction mixture. The reaction mixture is then subjected to a contemporaneous amplification and ligation reaction after which the reaction mixture is subjected to a separation process and thereby distinguishing an amplified target sequence, when present, wherein the target sequence is an STR locus. In some embodiments the STR locus is anyone of the STR loci CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement.

Primers are disclosed. "Primer" refers to an isolated oligonucleotide that can selectively hybridize to a complementary nucleic acid strand and allows for template directed synthesis of a polynucleotide. The synthesis can take place in the presence of an appropriate enzyme, cofactor and substrates.

Primers can be mechanically synthesized. During cellular DNA replication short, newly produced DNA polynucleotides are formed. These naturally occurring DNA polynucleotides are called Okazaki fragments. Mechanically synthesized primers can differ from these naturally occurring Okazaki fragments by the absence of a 5' phosphate or by the presence of modifications, such as a label. These differences render mechanically synthesized primers chemically and functionally distinct from Okazaki fragments. For instance, the absence of a 5' phosphate would hinder the ligation of Okazaki fragments. And Okazaki fragments can contain ribonucleic acids (RNA).

A primer pair refers to two primers that are the reverse complement of opposite strands of a double stranded polynucleotide.

Thus, in some embodiments a method is disclosed wherein a sample, a first synthetic primer, a synthetic second primer and a prolongation template are combined along with amplification and ligation reactants to form a reaction mixture. The reaction mixture is then subjected to a contemporaneous amplification and ligation reaction after which the reaction mixture is subjected to a separation process and thereby distinguishing an amplified target sequence, if any. In some embodiments, the method encompasses DNA in the reaction mixture. In some embodiments, the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than the second primer.

"Detectable Label" refers to moieties that be attached to nucleotides directly or indirectly to thereby render the molecule detectable by an instrument or method. For example, a label can be a moiety that: (i) provides a detectable signal or (ii) interacts with a second label to modify the detectable signal provided by the first or second label. Many different species of labels can be used, either individually or in combination with one or more different labels. A fluorophore is an example of a label.

Accordingly, in some embodiments a method is disclosed wherein a sample, a first primer, a second primer and a prolongation template are combined along with amplification and ligation reactants to form a reaction mixture, wherein the first, the second or the first and the second primers are detectably labeled. The reaction mixture is then subjected to a contemporaneous amplification and ligation reaction after which the reaction mixture is subjected to a separation process and thereby distinguishing an amplified target sequence, if any. In some embodiments, the method encompasses DNA in the reaction mixture. In some embodiments, the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than the second primer.

"Fluorophore" refers to a moiety that is inherently fluorescent or demonstrates a change in fluorescence upon binding to a biological compound or metal ion, or when metabolized by an enzyme. Numerous fluorophores are known, examples of which include coumarins, acridines, furans, dansyls, cyanines, pyrenes, naphthalenes, benzofurans, quinolines, quinazolinones, indoles, benzazoles, borapolyazaindacenes, oxazines and xanthenes, with the latter including fluoresceins, rhodamines, rosamines and rhodols.

Examples of fluorescent dyes, without limitation, include the following: 5- or 6-carboxyfluorescein (FAM™), VIC™, NED™, TAZ™, SID™, JOE™, TMR-ET, CXR-ET, BTG, BTY, BTR2, BTP, BTO, fluorescein, fluorescein isothiocyanate (FITC), IRD-700/800, cyanine dyes, such as CY3™, CY5™, CY3.5™, CY5.5™, Cy7™, xanthen, 6-carboxy-2', 4',7',4,7-hexachlorofluorescein (HEX™), 6-carboxy-1,4-dichloro-2',7'-dichloro-fluorescein (TET®), 6-carboxy-4',5'-dichloro-2',7'-dimethodyfluorescein (JOE™), N,N,N',N'-tetramethyl-6-carboxyrhodamine (TAMRA™), 6-carboxy-X-rhodamine (ROX™), 5-carboxyrhodamine-60 (R6G5), 6-carboxyrhodamine-6G (RG6), rhodamine, rhodamine green, rhodamine red, rhodamine 110, Rhodamin 6G®, BODIPY dyes, such as BODIPY TMR, oregon green, coumarines, such as umbelliferone, benzimides, such as Hoechst 33258; phenanthridines, such as Texas Red®, California Red®, Yakima Yellow, Alexa Fluor® 350, Alexa Fluor@ 405, Alexa Fluor® 430, Alexa Fluor® 488, Alexa Fluor® 500, Alexa Fluor® 514, Alexa Fluor®532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor@ 680, Alexa Fluor® 700, Alexa Fluor® 750, PET®, ethidium bromide, acridinium dyes, carbazol dyes, phenoxazine dyes, porphyrine dyes, polymethin dyes, Atto 390, Atto 425, Atto 465, Atto 488, Atto 495, Atto 520, Atto 532, Atto 550, Atto 565, Atto 590, Atto 594, Atto 620, Atto 633, Atto 647N, Atto 655, Atto RhoG6, Atto Rhol 1, Atto Rhol2, Atto Rhol01, BMN™-5, BMN™-6, CEQ8000 D2, CEQ8000 D3, CEQ8000 D4, DY-480XL, DY-485XL, DY-495, DY-505, DY-510XL, DY-521XL, DY-521XL, DY-530, DY-547, DY-550, DY-555, DY-610, DY-615, DY-630, DY-631, DY-633, DY-635, DY-647, DY-651, DY-675, DY-676, DY-680, DY-681, DY-700, DY-701, DY-730, DY-731, DY-732, DY-750, DY-751, DY-776, DY-780, DY-781, DY-782, CAL Fluor® Gold 540, CAL Fluor RED 590, CAL Fluor Red 610, CAL Fluor Red 635, IRDye® 700Dx, IRDye® 800CW, Marina Blue®, Pacific Blue®, Yakima Yellow®, 6-(4,7-Dichloro-2',7'-diphenyl-3',6'-dipivaloyl-fluorescein-6-carboxamido)-hexyl-1-0-(2-cyanoethyl)-(N,N-diisopropyl)-phosphoramidite (SIMA), CAL Fluor® Gold 540, CAL Fluor® Orange 560, CAL Fluor Red 635, Quasar® 570, Quasar® 670, LIZ, Sunnyvale Red, LC Red® 610, LC Red® 640, LC Red®670 and LC Red®705.

In some embodiments a method is disclosed wherein a sample, a first primer, a second primer and a prolongation template are combined along with amplification and ligation reactants to form a reaction mixture, wherein the first, the second or the first and the second primers are labeled with a fluorophore. In other embodiments, the first, the second or the first and the second primers are labeled with a fluorescent dye. The reaction mixture is then subjected to a contemporaneous amplification and ligation reaction after which the reaction mixture is subjected to a separation process and thereby distinguishing an amplified target sequence, if any. In some embodiments, the method encompasses DNA in the reaction mixture. In some embodiments the first, the second or the first and the second primers are synthetic. In some embodiments, the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than the second primer. In some embodiments the prolongation template is labeled with a fluorophore. In other embodiments the prolongation template is labeled with a fluorophore but the first primer and the second primer are not. In some embodiments, the prolongation template is labeled with a fluorophore and one of the primers is labeled with a fluorophore. In other embodiments, the prolongation template is labeled with a fluorophore and each of the primers is labeled with a fluorophore. In some embodiments, the prolongation template is not labeled with at fluorophore dye. In some embodiments the prolongation template is labeled with a fluorescent dye. In other embodiments the prolongation template is labeled with a fluorescent dye but the first primer and the second primer are not. In some embodiments, the prolongation template is labeled with a fluorescent dye and one of the primers is labeled with a fluorescent dye. In other embodiments, the prolongation template is labeled with a fluorescent dye and each of the primers is labeled with a fluorescent dye. In some embodiments, the prolongation template is not labeled with at fluorescent dye.

"Affinity label" refers to a moiety that specifically binds to a target molecule so that the target molecule can be captured, tracked or identified. Non-limiting examples of an affinity label are biotin, avidin, an antibody, an antigen, a receptor, a substrate, a lectin, an aptamer, a magnetically attractable solid support, or a magnet.

In some embodiments a method is disclosed wherein a sample, a first primer, a second primer and a prolongation template are combined along with amplification and ligation reactants to form a reaction mixture, wherein the first, the second or the first and the second primers are labeled with an affinity label. In other embodiments, the first, the second or the first and second primers are labeled with biotin. The reaction mixture is then subjected to a contemporaneous amplification and ligation reaction after which the reaction mixture is subjected to a separation process and thereby distinguishing an amplified target sequence, if any. In some embodiments, the method encompasses DNA in the reaction mixture. In some embodiments the first, the second or the first and the second primers are synthetic. In some embodiments, the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than the second primer. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

The instant disclosure provides for a prolongation template. A "prolongation template" is a polynucleotide a portion of which hybridizes to a target sequence that is 5' of a first primer binding site and a portion of which hybridizes to another primer. That is, if a primer were extended in a template dependent fashion from 5' to 3', the extension product would extend towards the 5' end of the prolongation template, while a second primer hybridization site is present in the prolongation template. In some instances, the prolongation template can, over its entire length, be the reverse complement to a sequence flanking the target sequence. In other instances, the prolongation template can encompass two regions, a sequence region that is the reverse complement of a sequence flanking the target sequence, referred to as the complementary prolongation template region, and a sequence region that is not complementary to a sequence flanking the target sequence, referred to as the non-complementary prolongation template region. In some instances, the second primer is the reverse complement to a sequence within the complementary prolongation template region. In some instances, the second primer is the reverse complement to a sequence within the non-complementary prolongation template region.

The prolongation template can be a polynucleotide of at least 20 nucleotides in length. The prolongation template can be a polynucleotide of at least 21, 22, 23, 24, 25, 26, 27, 28, 29, 30 or more nucleotides in length. The prolongation template can be a polynucleotide with a length of any integer from 31-1000 nucleotides. The prolongation template can be a polynucleotide of less than 1000, less than 900, less than 800, less than 700, less than 600, less than 500, less than 400, less than 300, less than 200, less than 100, less than 90, less than 80, less than 70 nucleotides in length. The prolongation template can be from 20-500, 20-400, 20-300, 20-200 or 20-100 nucleotides in length.

The complementary prolongation template region can be a polynucleotide of at least 20 nucleotides in length. The complementary prolongation template region can be a polynucleotide of at least 21, 22, 23, 24, 25, 26, 27, 28, 29, 30 or more nucleotides in length. The non-complementary prolongation template region can be a polynucleotide with a length of any integer from 31-980 nucleotides. The complementary prolongation template region can be a polynucleotide of less than 1000, less than 900, less than 800, less than 700, less than 600, less than 500, less than 400, less than 300, less than 200, less than 100, less than 90, less than 80, less than 70 nucleotides in length. The complementary prolongation template region can be from 20-500, 20-400, 20-300, 20-200 or 20-100 nucleotides in length.

The non-complementary prolongation template region can be a polynucleotide of at least 20 nucleotides in length. The non-complementary prolongation template region can be a polynucleotide of at least 21, 22, 23, 24, 25, 26, 27, 28, 29, 30 or more nucleotides in length. The non-complementary prolongation template region can be a polynucleotide with a length of any integer from 31-980 nucleotides. The non-complementary prolongation template region can be a polynucleotide of less than 1000, less than 900, less than 800, less than 700, less than 600, less than 500, less than 400, less than 300, less than 200, less than 100, less than 90, less than 80, less than 70 nucleotides in length. The non-complementary prolongation template region can be from 20-500, 20-400, 20-300, 20-200 or 20-100 nucleotides in length.

In some instances, the second primer can hybridize to the 3' most end of the prolongation template, such that the 5' nucleotide of the second primer hybridizes with the 3' end of the prolongation template. In some instances the second primer hybridizes to the prolongation internally such that the 5' nucleotide of the second primer hybridizes at least one or more nucleotides from the 3' end of the prolongation template.

In some instances, the 3' end of the first primer may abut the 5' end of the prolongation template. In other instances, the 3' end of the first primer does not abut the 5' end of the prolongation template. Accordingly, in some instances, the 3' end of the first primer must be extended by the addition of least one, at least two, at least three, at least four, at least five, at least six, at least seven, at least eight, at least nine, at least ten or more nucleotides before the 3' of the first primer abuts the 5' end of the prolongation template. In some instances, the first primer is extended from 11-2,000 nucleotides before the 3' end of the first primer abuts the 5' end of the prolongation template. In other instances, the first primer is extended by 11-1,000 nucleotides before the 3' end of the first primer abuts the 5' end of the prolongation template. In some instances, the first primer is extended by 11-500, 11-450, 11-400, 11-350, 11-300, 11-250, 11-200, 11-150, 11-100, 11-90, 11-80, 11-70, 11-60, 11-50, 11-40, 11-30, or 11-20 nucleotides before the 3' end of the first primer abuts the 5' end of the prolongation template.

In some instances, the extension requires the presence of nucleosides that are the reverse complement of the bases adenine, guanine, cytosine and thymine. In other instances, the extension does not require the presence of nucleosides that are the reverse complement of one or more of adenine or guanine or cytosine or thymine.

Accordingly, in some embodiments a method is disclosed wherein a sample, a first primer, a second primer and a prolongation template are combined along with amplification and ligation reactants to form a reaction mixture, wherein the reaction mixture further encompasses adenosine triphosphate, cytidine triphosphate, guanosine triphosphate and thymidine triphosphate. In some embodiments a method is disclosed wherein a sample, a first primer, a second primer and a prolongation template are combined along with amplification and ligation reactants to form a reaction mixture, wherein the reaction mixture encompasses one, two or three of the following nucleosides adenosine triphosphate, cytidine triphosphate, guanosine triphosphate and thymidine triphosphate but not all four. The reaction mixture is then subjected to a contemporaneous amplification and ligation reaction after which the reaction mixture is subjected to a separation process and thereby distinguishing the amplified target sequence, if any. In some embodiments, the method encompasses DNA in the reaction mixture. In some embodiments the first, the second or the first and the second primers are synthetic. In some embodiments, the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than the second primer. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

TABLE 1

Sequences of Primers and Prolongation Template

| Locus | Primer | Partial Prolongation Template Sequence |
|---|---|---|
| CSF1PO | 1:ACAGTAACTGCCTTCATAGATAG (SEQ ID NO. 6) | 1:TACTTAGAACAGGGTCTGACAC (SEQ ID NO. 7) |
| | 2:GTGTCAGACCCTGTTCTAAGTA (SEQ ID NO. 8) | 2:CTATCTATGAAGGCAGTTACTG (SEQ ID NO. 9) |
| FGA | 1:AAATAAAATTAGGCATATTTACAAGC (SEQ ID NO. 10) | 1:CAATTACAGACAATCACTCAGC (SEQ ID NO. 11) |
| | 2:GCTGAGTGATTTGTCTGTAATTG (SEQ ID NO. 12) | 2:GCTTGTAAATATGCCTAATTTTATT (SEQ ID NO. 13) |

TABLE 1-continued

Sequences of Primers and Prolongation Template

| Locus | Primer | Partial Prolongation Template Sequence |
|---|---|---|
| TH01 | 1:CCTGTTCCTCCCTTATTTCCC (SEQ ID NO. 14)<br>2:GGGAACACAGACTCCATGGTG (SEQ ID NO.16 ) | 1:CACCATGGAGTCTGTGTTCCC(SEQ ID NO. 15)<br>2:GGGAAATAAGGGAGGAACAGG (SEQ ID NO. 17) |
| TPDX | 1:CTTAGGGAACCCTCACTGAATG (SEQ ID NO. 18)<br>2:GTCCTTGTCAGCGTTTATTTG C (SEQ ID NO. 20) | 1:GCAAATAAACGCTGACAAGGAC (SEQ ID NO. 19)<br>2:CATTCAGTGAGGGTTCCCTAAG (SEQ ID NO. 21) |
| vWA | 1:AATAATCAGTATGTGACTTGG ATTGA (SEQ ID NO. 22)<br>2:ATAGGATGGATGGATAGATG GA (SEQ ID NO. 24) | 1:TCCATCTATCCATCCATCCTAT(SEQ ID NO. 23)<br>2:TCAATCCAAGTCACATACTCATTA TT (SEQ ID NO. 25) |
| D3S1358 | 1:CAGAGCAAGACCCTGTCTCAT (SEQ ID NO. 26)<br>2:TCAACAGAGGCTTGCATGTAT (SEQ ID NO. 28) | 1:ATACATGCAAGCCTCTGTTGA (SEQ ID NO. 27)<br>2:ATGAGACAGGGTCTTGCTCTG (SEQ ID NO. 29) |
| D5S818 | 1:GGGTGATTTTCCTCTTTGGT (SEQ ID NO. 30)<br>2:AACATTTGTATCTTTATCTGT ATCCTTATTTAT (SEQ ID NO. 32) | 1:ATAAATAAGGATACAGATAAAGAT ACAAATGTT (SEQ ID NO. 31)<br>2:ACCAAAGAGGAAAATCACCC (SEQ ID NO. 33) |
| D7S 820 | 1:GAACACTTGTCATAGTTTAGA ACGAAC (SEQ ID NO. 34)<br>2:TCATTGACAGAATTGCACCA (SEQ ID NO. 36) | 1:TCATTGACAGAATTGCACCA (SEQ ID NO. 35)<br>2:TGGTGCAATTCTGTCAATGA (SEQ ID NO. 37) |
| D8S1179 | 1:TTTGTATTTCATGTGTACATTC GTATC (SEQ ID NO. 38)<br>2:ACCTATCCTGTAGATTATTTT CACTGTG (SEQ ID NO. 40) | 1:CACAGTGAAAATAATCTACAGGAT AGGT(SEQ ID NO. 39)<br>2:GATACGAATGTACACATGAAATAC AAA (SEQ ID NO. 41) |
| D13S317 | 1:TCTGACCCATCTAACGCCTA (SEQ ID NO. 42)<br>2:CAGACAGAAAGATAGATAGA TGATTGA (SEQ ID NO. 44) | 1:TCAATCATCTATCTATCTTTCTGTC TG (SEQ ID NO. 43)<br>2:TAGGCGTTAGATGGGTCAGA (SEQ ID NO. 45) |
| D16S539 | 1:ATACAGACAGACAGACAGGT G (SEQ ID NO. 46)<br>2:GCATGTATCTATCATCCATCT CT (SEQ ID NO. 48) | 1:AGAGATGGATGATAGATACATGC (SEQ ID NO. 47)<br>2:CACCTGTCTGTCTGTCTGTAT (SEQ ID NO. 49) |
| D18551 | 1:TGAGTGACAAATTGAGACCTT (SEQ ID NO. 50)<br>2:GTCTTACAATAACAGTTGCTA CTATT (SEQ ID NO. 52) | 1:AATAGTAGCAACTGTTATTGTAAG AC (SEQ ID NO. 51)<br>2:AAGGTCTCAATTTGTCACTCA (SEQ ID NO. 53) |
| D21S11 | 1:ATTCCCCAAGTGAATTGC (SEQ ID NO. 54)<br>2:GGTAGATAGACTGGATAGAT AGACGA (SEQ ID NO. 56) | 1:TCGTCTATCTATCCAGTCTATCTAC C (SEQ ID NO. 55)<br>2:GCAATTCACTTGGGGAAT (SEQ ID NO. 57) |
| Penta D | 1:GAGCAAGACACCATCTCAAG AA (SEQ ID NO. 58)<br>2:GAAATTTTACATTTATGTTTA TGATTCTCT (SEQ ID NO. 60) | 1:AGAGAATCATAAACATAAATGTAA AATTTC(SEQ ID NO. 59)<br>2:TTCTTGAGATGGTGTCTTGCTC (SEQ ID NO. 61) |
| Penta E | 1:GGCGACTGAGCAAGACTC (SEQ ID NO. 62)<br>2:GGTTATTAATTGAGAAAACTC CTTACA (SEQ ID NO. 64) | 1:TGTAAGGAGTTTTCTCAATTAATA ACC (SEQ ID NO. 63)<br>2:GAGTCTTGCTCAGTCGCC (SEQ ID NO. 65) |
| D2S1338 | 1:TGGAAACAGAAATGGCTTGG (SEQ ID NO. 66)<br>2:GATTGCAGGAGGGAAGGAAG (SEQ ID NO. 68) | 1:CTTCCTTCCCTCCTGCAATC (SEQ ID NO. 67)<br>2:CCAAGCCATTTCTGTTTCCA (SEQ ID NO. 69) |

In some embodiments, a method is disclosed wherein a sample, a first primer, a second primer and a prolongation template are combined along with amplification and ligation reactants to form a reaction mixture, wherein the first primer encompasses one of the sequences listed under "Primer" in Table 1. In other embodiments, the prolongation template can encompass one of the sequences listed under "Partial Prolongation Template Sequence" in Table 1. The reaction mixture is then subjected to a contemporaneous amplification and ligation reaction after which the reaction mixture is subjected to a separation process and thereby distinguishing the amplified target sequence, if any. In some embodiments, the method encompasses DNA in the reaction mixture.

Polymerases

A primer can be extended by a polymerase. A "polymerase" is an enzyme that catalyzes the polymerization of a nucleotide. A DNA polymerase catalyzes the polymerization of deoxynucleotides.

In some embodiments a method is disclosed wherein a sample, a first primer, a second primer and a prolongation template are combined along with amplification and ligation reactants to form a reaction mixture, wherein the amplification reactants encompass a polymerase. The reaction mixture is then subjected to a contemporaneous amplification and ligation reaction after which the reaction mixture is subjected to a separation process and thereby distinguishing the amplified target sequence, if any. In some embodiments, the method encompasses DNA in the reaction mixture. In some embodiments the first, the second or the first and the second primers are synthetic. In some embodiments the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

In some embodiments a method is disclosed wherein a sample, a first primer, a second primer and a prolongation template are combined along with amplification and ligation reactants to form a reaction mixture, wherein the amplification reactants encompass a DNA polymerase. The reaction mixture is then subjected to a contemporaneous amplification and ligation reaction after which the reaction mixture is subjected to a separation process and thereby distinguishing the amplified target sequence, if any. In some embodiments, the method encompasses DNA in the reaction mixture. In some embodiments the first, the second or the first and the second primers are synthetic. In some embodiments the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

In some embodiments a method is disclosed wherein a sample, a first primer, a second primer and a prolongation template are combined along with amplification and ligation reactants to form a reaction mixture, wherein the amplification reactants encompass a DNA polymerase and the reaction mixture further encompasses adenosine triphosphate, cytidine triphosphate, guanosine triphosphate and thymidine triphosphate. In some embodiments a method is disclosed wherein a sample, a first primer, a second primer and a prolongation template are combined along with amplification and ligation reactants to form a reaction mixture, wherein the reaction mixture encompasses one, two or three of the following nucleosides adenosine triphosphate, cytidine triphosphate, guanosine triphosphate and thymidine triphosphate but not all four. The reaction mixture is then subjected to a contemporaneous amplification and ligation reaction after which the reaction mixture is subjected to a separation process and thereby distinguishing the amplified target sequence, if any. In some embodiments, the method encompasses DNA in the reaction mixture. In some embodiments the first, the second or the first and the second primers are synthetic. In some embodiments the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

A feature that distinguishes DNA polymerases is the capacity to strand displace. "Strand displacement activity" refers to the ability to dissociate nucleic acid sequences from their reverse complement when the nucleic acid sequence is encountered downstream from the point of nucleic acid synthesis initiation. Strand displacement begins at the 5' end of the encountered nucleic acid and is propagated in a 5' to 3' direction. Some DNA polymerases possess strand displacement capacity, for example *E. coli* DNA polymerase I, large (Klenow) fragment. Other DNA polymerases however exhibit relatively poor strand displacement activity or apparently lack any strand displacement activity at all. Examples of DNA polymerases that are reported to have poor or lack strand displacement activity include Sulfolubus DNA polymerase IV, T4, T7 (unmodified), polymerases isolated from *Thermococcus kodakaraensis, Thermococcus litoralis* and *Pyrococcus furiosis* and polymerases marketed under the tradenames Phusion® and Q5®.

A chart depicting the strand displacement activity of a number of commercially available DNA polymerases is provided by New England Biolabs at hypertext transfer protocol secure://world wide web.neb.com/tools-and-resources/selection-charts/dna-polymerase-selection-chart (last visited Jan. 22, 2015).

A methodology for elucidating the relative strand displacement activity of polymerases is described by Kong et al. (1993) "Characterization of a DNA Polymerase from the Hyperthermophile Archaea *Thermococcus litoralis" J. Biol. Chem.* 268(3):1965-1975. The described strand displacement activity assay involves a labeled primer, an oligonucleotide and a single stranded template. The number of nucleotides separating the 3' of the primer and the 5' end of the oligonucleotide are known. The primer and oligonucleotide are allowed to hybridize with the single stranded template. A polymerase whose strand displacement activity that is to be tested is added and polymerase mediated DNA synthesis occurs. The resulting DNA synthesis products are analyzed. The predominant synthesis product generated by polymerases with relatively reduced or absent strand displacement activity is the primer plus the number of nucleotides separating the 3' of the primer and the 5' end of the oligonucleotide. Polymerases with strand displacement activity produce products considerable longer than the primer plus the number of nucleotides separating the 3' of the primer and the 5' end of the oligonucleotide.

A "polymerase lacking strand displacement activity" refers to a polymerase wherein the majority of the product in the strand displacement assay, such as that described by Kong, is the primer plus the number of nucleotides separating the 3' of the primer and the 5' end of the oligonucleotide when the polymerase is tested under the conditions demonstrated to show the least strand displacement activity for that polymerase in the strand displacement assay.

For instance, for the *Thermococcus litoralis* polymerase taught by Kong, the percentage of product with the primer plus the number of nucleotides separating the 3' of the primer and the 5' end of the oligonucleotide would be determined based on the results of an assay at 55° C. and with the reagents and conditions disclosed.

Examples of polymerases in the literature identified to lack strand displacement activity are *E. coli* DNA polymerase I, large (Klenow) fragment, Stoffel fragment of Taq polymerase, Sulfolubus DNA polymerase IV, T4, T7 (unmodified), polymerases isolated from *Thermococcus kodakaraensis* and *Pyrococcus furiosis* and polymerases marketed under the tradenames Phusion® and Q5®.

A "polymerase with reduced strand displacement activity" refers to a polymerase wherein about 45%, about 40%, about 35%, about 30%, about 25%, about 20%, about 15%, about 10% of the product in the strand displacement assay, such as that described by Kong, is the primer plus the number of nucleotides separating the 3' of the primer and the 5' end of the oligonucleotide when the polymerase is tested under the conditions demonstrated to show the least strand displacement activity for that polymerase in the strand displacement assay.

In some embodiments a method is disclosed wherein a sample, a first primer, a second primer and a prolongation template are combined along with amplification and ligation reactants to form a reaction mixture, wherein the amplification reactants encompass a polymerase and the polymerase lacks strand displacement activity. The reaction mixture is then subjected to a contemporaneous amplification and ligation reaction after which the reaction mixture is subjected to a separation process and thereby distinguishing the amplified target sequence, if any.

In other embodiments a method is disclosed wherein a sample, a first synthetic primer, a synthetic second primer and a prolongation template are combined along with amplification and ligation reactants to form a reaction mixture, wherein the amplification reactants encompass a polymerase and the polymerase lacks strand displacement activity. The reaction mixture is then subjected to a contemporaneous amplification and ligation reaction after which the reaction mixture is subjected to a separation process and thereby distinguishing the amplified target sequence, if any.

In some embodiments a method is disclosed wherein a sample, a first primer, a second primer and a prolongation template are combined along with amplification and ligation reactants to form a reaction mixture, wherein the amplification reactants encompass a DNA polymerase and the DNA polymerase lacks strand displacement activity. The reaction mixture is then subjected to a contemporaneous amplification and ligation reaction after which the reaction mixture is subjected to a separation process and thereby distinguishing the amplified target sequence, if any. In some embodiments, the amplification reactants encompass a DNA polymerase and the DNA polymerase lacks strand displacement activity and the reaction mixture further encompasses adenosine triphosphate, cytidine triphosphate, guanosine triphosphate and thymidine triphosphate. In some embodiments a method is disclosed wherein a sample, a first primer, a second primer and a prolongation template are combined along with amplification and ligation reactants to form a reaction mixture, wherein the reaction mixture encompasses one, two or three of the following nucleosides adenosine triphosphate, cytidine triphosphate, guanosine triphosphate and thymidine triphosphate but not all four. The reaction mixture is then subjected to a contemporaneous amplification and ligation reaction after which the reaction mixture is subjected to a separation process and thereby distinguishing the amplified target sequence, if any. In some embodiments, the method encompasses DNA in the reaction mixture. In some embodiments the first, the second or the first and the second primers are synthetic. In some embodiments the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

An activity possessed by some polymerases is 5' to 3' exonuclease activity; the ability to cleave nucleotides from the 5' end of a polynucleotide chain. An example of a DNA polymerase that lacks 5' to 3' exonuclease activity is *E. coli* DNA polymerase I, large (Klenow) fragment. On the other hand Taq DNA polymerase possesses 5' to 3' exonuclease activity. A chart depicting the 5' to 3' exonuclease activity of a number of commercially available DNA polymerases is provided by New England Biolabs at hypertext transfer protocol secure://world wide web.neb.com/tools-and-resources/selection-charts/dna-polymerase-selection-chart (last visited Jan. 22, 2015).

As with strand displacement activity, Kong describes a methodology for assessing the 5' to 3' exonuclease activity of a polymerase. To assay the directionality of nuclease activity, a linear DNA substrate is prepared with differential terminal labels. The labeled substrate is incubated in the presence of the polymerase. By monitoring the relative solubilization of the two labels it is possible to determine whether the polymerase has exonuclease activity and its directionality 5' to 3' or 3' to 5'.

Table 2 summarizes the 5' to 3' exonuclease activity and the strand displacement activity of a number of polymerases. Kong tested and observed the exonuclease activity, and the directionality of that activity, for three polymerases Tli (Vent, See Kong Abstract), Taq and DNA Polymerase I. In Kong's assay, a polymerase lacks apparent 5' to 3' exonuclease activity if at least 60% of the 3' label is released before 10% of the 5' label is released. Based on this assay, Tli lacks 5' to 3' exonuclease activity.

TABLE 2

| | 5' → 3' Exonuclease Activity | Strand Displacement Activity |
|---|---|---|
| Bst DNA Polymerase, Full Length | + | Degrades encountered polynucleotide |
| Bst DNA Polymerase, Large Fragment | — | ++++ |
| Bsu DNA Polymerase, Large Fragment | — | ++ |
| Crimson Taq DNA Polymerase | + | Degrades encountered polynucleotide |
| Deep Vent$_R$ ™ DNA Polymerase | — | ++ |
| Deep Vent$_R$ ™ (exo-)DNA Polymerase | — | +++ |
| E. coli DNA Polymerase I | + | Degrades encountered polynucleotide |
| Klenow Fragment (3' → 5' exo-) | — | +++ |
| DNA Polymerase I, Large (Klenow) Fragment | — | ++ |
| LongAmp ® Taq DNA Polymerase | + | Degrades encountered polynucleotide |
| LongAmp ® Hot Start Taq DNA Polymerase | + | Degrades encountered polynucleotide |
| M-MuLV Reverse Transcriptase | — | +++ |
| One Taq ® DNA Polymerase | + | Degrades encountered polynucleotide |
| One Taq ® Hot Start DNA Polymerase | + | Degrades encountered polynucleotide |
| Phi29 DNA Polymerase | — | +++++ |
| Phusion ® Hot Start Flex DNA Polymerase | — | — |
| Phusion ® High - Fidelity Flex DNA Polymerase | — | — |
| Q5 ® + Q5 ® Hot Start DNA Polymerase | — | — |
| Sulfolobus DNA Polymerase IV | — | — |
| T4 DNA Polymerase | — | — |
| T7 DNA Polymerase (unmodified) | — | — |
| Taq DNA Polymearse with Standard Taq Buffer | + | Degrades encountered polynucleotide |
| Terminator ™ DNA Polymerase | — | + |
| Vent$_R$ ® DNA Polymerase | — | ++ |
| Vent$_R$ ® (exo-)DNA Polymerase | — | +++ |

Table 2 provides the relative capacity of different polymerases to displace encountered polynucleotides. For instance, Vent$_R$® DNA Polymerase is the polymerase tested in the assay described by Kong (See Abstract). Thus, the data in the strand displacement assay described by Kong is associated with a polymerase possessing about ++/+++ strand displacement activity.

Accordingly, in some embodiments a method is disclosed wherein a sample, a first primer, a second primer and a prolongation template are combined along with amplification and ligation reactants to form a reaction mixture, wherein the amplification reactants encompass a polymerase and the polymerase lacks strand displacement activity and lacks 5' to 3' exonuclease activity. The reaction mixture is then subjected to a contemporaneous amplification and ligation reaction after which the reaction mixture is subjected to a separation process and thereby distinguishing the amplified target sequence, if any. In some embodiments, the amplification reactants encompass a DNA polymerase and the DNA polymerase lacks strand displacement activity and lacks 5' to 3' exonuclease activity and the reaction mixture further encompasses adenosine triphosphate, cytidine triphosphate, guanosine triphosphate and thymidine triphosphate. In some embodiments a method is disclosed wherein a sample, a first primer, a second primer and a prolongation template are combined along with amplification and ligation reactants to form a reaction mixture, wherein the reaction mixture encompasses one, two or three of the following nucleosides adenosine triphosphate, cytidine triphosphate, guanosine triphosphate and thymidine triphosphate but not all four. The reaction mixture is then subjected to a contemporaneous amplification and ligation reaction after which the reaction mixture is subjected to a separation process and thereby distinguishing the amplified target sequence, if any. In some embodiments, the method encompasses DNA in the reaction mixture. In some embodiments the first, the second or the first and the second primers are synthetic. In some embodiments the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

Disclosed herein are ligases. "Ligation" refers to the formation of a phosphodiester linkage between the 3' terminus and the 5' terminus of nucleic acid sequences. Ligation can be accomplished with an enzyme referred to as a "ligase." Examples of ligases include Taq DNA ligase, Tina DNA ligase, *Thermus thermophiles* (Tth) DNA ligase, *Thermus scotodus* (Ts) DNA ligase, *Rhodothermus marinus* (Rm) DNA ligase, *Thermus filiformis* DNA ligase, Pfu DNA ligase, *Thermococcus* 9° N and the ligase sold under the trade name Ampligase® Thermostable DNA ligase. Certain DNA ligases are thermostable, maintaining their catalytic activity at temperatures above 42° C., even at temperatures ranging from 90-100° C.

Accordingly, in some embodiments a method is disclosed wherein a sample, a first primer, a second primer and a prolongation template are combined along with amplification and ligation reactants to form a reaction mixture, wherein the amplification reactants encompass a polymerase and the polymerase lacks strand displacement activity and the ligation reactants encompass a ligase. In some embodiments the amplification reactants encompass a polymerase and the polymerase lacks strand displacement activity and lacks 5' to 3' exonuclease activity and the ligation reactants encompass a ligase. In some embodiments the ligase is a thermostable ligase. In other embodiments the thermostable ligase is Taq DNA ligase. The reaction mixture is then subjected to a contemporaneous amplification and ligation reaction after which the reaction mixture is subjected to a separation process and thereby distinguishing the amplified target sequence, if any. In some embodiments, the sample encompassed DNA. In some embodiments the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

In other embodiments a method is disclosed wherein a sample, a first synthetic primer, a synthetic second primer and a prolongation template are combined along with amplification and ligation reactants to form a reaction mixture, wherein the amplification reactants encompass a polymerase and the polymerase lacks strand displacement activity and the ligation reactants encompass a ligase. In some embodiments the amplification reactants encompass a polymerase and the polymerase lacks strand displacement activity and lacks 5' to 3' exonuclease activity and the ligation reactants encompass a ligase. In some embodiments the ligase is a thermostable ligase. In other embodiments the thermostable ligase is Taq DNA ligase. The reaction mixture is then subjected to a contemporaneous amplification and ligation reaction after which the reaction mixture is subjected to a separation process and thereby distinguishing the amplified target sequence, if any. In some embodiments, the sample encompassed DNA. In some embodiments the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

In some embodiments a method is disclosed wherein a sample, a first primer, a second primer and a prolongation template are combined along with amplification and ligation reactants to form a reaction mixture, wherein the amplification reactants encompass a polymerase and the polymerase lacks strand displacement activity and the ligation reactants encompass a ligase. In some embodiments the amplification reactants encompass a polymerase and the polymerase lacks strand displacement activity and lacks 5' to 3' exonuclease activity and the ligation reactants encompass a ligase. In some embodiments the ligase is a thermostable ligase. In other embodiments the thermostable ligase is Taq DNA ligase. The reaction mixture is then subjected to a contemporaneous amplification and ligation reaction after which the reaction mixture is subjected to a separation process and thereby distinguishing the amplified target sequence, if any. In some embodiments, the sample possesses DNA. In some embodiments the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

In some embodiments a method is disclosed wherein a sample, a first primer, a second primer and a prolongation template are combined along with amplification and ligation reactants to form a reaction mixture, wherein the amplification reactants encompass a polymerase and the polymerase lacks strand displacement activity and the ligation reactants encompass a ligase. In some embodiments the amplification reactants encompass a polymerase and the polymerase lacks strand displacement activity and lacks 5' to 3' exonuclease activity and the ligation reactants encompass a ligase. In some embodiments the ligase is a thermostable ligase. In other embodiments the thermostable ligase is Taq DNA ligase. In some embodiments the reaction mixture further encompasses adenosine triphosphate, cytidine triphosphate, guanosine triphosphate and thymidine triphosphate. The reaction mixture is then subjected to a contemporaneous amplification and ligation reaction after which the reaction mixture is subjected to a separation process and thereby distinguishing the amplified target sequence, if any. In some embodiments, the sample possesses DNA. In some embodiments the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21511, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

In other embodiments a method is disclosed wherein a sample, a first synthetic primer, a synthetic second primer and a prolongation template are combined along with amplification and ligation reactants to form a reaction mixture, wherein the amplification reactants encompass a polymerase and the polymerase lacks strand displacement activity and the ligation reactants encompass a ligase. In some embodiments the amplification reactants encompass a polymerase and the polymerase lacks strand displacement activity and lacks 5' to 3' exonuclease activity and the ligation reactants encompass a ligase. In some embodiments the ligase is a thermostable ligase. In other embodiments the thermostable ligase is Taq DNA ligase. In some embodiments the reaction mixture further encompasses adenosine triphosphate, cytidine triphosphate, guanosine triphosphate and thymidine triphosphate. The reaction mixture is then subjected to a contemporaneous amplification and ligation reaction after which the reaction mixture is subjected to a separation process and thereby distinguishing the amplified target sequence, if any. In some embodiments, the sample possesses DNA. In some embodiments the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

Capillary Electrophoresis

An electrophoretic technique is capillary electrophoresis (CE). In CE, a specimen is introduced to an end of a narrow capillary tube filled with a polymer solution. The polymer solution serves as a sieving matrix.

Electrophoresis uses the combination of an electrical field with a sieving matrix to separate nucleic acid species. With polynucleotides, the phosphate group of each nucleotide unit carries a relatively strong negative charge, much stronger than any charges on the bases. For this reason, the mass-to-charge ratio of the polynucleotides is largely independent of the base composition.

In the presence of an electrical field a DNA molecule that is 10 nucleotides long will experience relatively the same force pulling on as a DNA molecule 100 nucleotides long. Therefore, to separate nucleic acid species based on length electrophoretically requires that the nucleic species be passed through a sieving matrix that retards mobility. The progress of larger species through the matrix is slower than smaller molecules. In this way, smaller species migrate ahead of larger species as electrophoresis proceeds.

Detection of the separated nucleic acid species in CE is routinely performed by detecting laser induced fluorescence at a fixed position along the capillary. Fluorescently labeled primers are used to amplify the nucleic acid species. Smaller labeled nucleic acid species arrive at the detection point first followed by larger labeled nucleic acid species. By differentially labeling the primers, and in turn the amplified species, multiple loci can be analyzed in the same capillary. The use of different dyes allows even for resolving two different nucleic acid species that migrate at the same rate.

Accordingly, in some embodiments a method is disclosed wherein a sample, a first primer, a second primer and a prolongation template are combined along with amplification and ligation reactants to form a reaction mixture, wherein the amplification reactants encompass a polymerase and the polymerase lacks strand displacement activity and the ligation reactants encompass a ligase. In some embodiments the amplification reactants encompass a polymerase and the polymerase lacks strand displacement activity and lacks 5' to 3' exonuclease activity and the ligation reactants encompass a ligase. In some embodiments the ligase is a thermostable ligase. In other embodiments the thermostable ligase is Taq DNA ligase. The reaction mixture is then subjected to a contemporaneous amplification and ligation reaction after which the reaction mixture is subjected to a separation process and thereby distinguishing the amplified target sequence, if any. In some embodiments, the sample encompassed DNA. In some embodiments the separation process is electrophoresis. In other embodiments electrophoresis is capillary electrophoresis. In some embodiments a method is disclosed wherein a sample, a first primer, a second primer and a prolongation template are combined along with amplification and ligation reactants to form a reaction mixture, wherein the reaction mixture encompasses one, two or three of the following nucleosides adenosine triphosphate, cytidine triphosphate, guanosine triphosphate and thymidine triphosphate but not all four. The reaction mixture is then subjected to a contemporaneous amplification and ligation reaction after which the reaction mixture is subjected to a separation process and thereby distinguishing the amplified target sequence, if any. In some embodiments, the method encompasses DNA in the reaction mixture. In some embodiments the first, the second or the first and the second primers are synthetic. In some embodiments the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

In other embodiments a method is disclosed wherein a sample, a first synthetic primer, a synthetic second primer and a prolongation template are combined along with amplification and ligation reactants to form a reaction mixture, wherein the amplification reactants encompass a polymerase and the polymerase lacks strand displacement activity and the ligation reactants encompass a ligase. In some embodiments the amplification reactants encompass a polymerase and the polymerase lacks strand displacement activity and lacks 5' to 3' exonuclease activity and the ligation reactants encompass a ligase. In some embodiments the ligase is a thermostable ligase. In other embodiments the thermostable ligase is Taq DNA ligase. The reaction mixture is then subjected to a contemporaneous amplification and ligation reaction after which the reaction mixture is subjected to a separation process and thereby distinguishing the amplified target sequence, if any. In some embodiments a method is disclosed wherein a sample, a first primer, a second primer and a prolongation template are combined along with amplification and ligation reactants to form a reaction mixture, wherein the reaction mixture encompasses one, two or three of the following nucleosides adenosine triphosphate, cytidine triphosphate, guanosine triphosphate and thymidine triphosphate but not all four. The reaction mixture is then subjected to a contemporaneous amplification and ligation reaction after which the reaction mixture is subjected to a separation process and thereby distinguishing the amplified target sequence, if any. In some embodiments, the method encompasses DNA in the reaction mixture. In some embodiments the first, the second or the first and the second primers are synthetic. In some embodiments the separation process is electrophoresis. In other embodiments electrophoresis is capillary electrophoresis. In some embodiments the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

In some embodiments a method is disclosed wherein a sample, a first primer, a second primer and a prolongation template are combined along with amplification and ligation reactants to form a reaction mixture, wherein the amplification reactants encompass a polymerase and the polymerase lacks strand displacement activity and the ligation reactants encompass a ligase. In some embodiments the amplification reactants encompass a polymerase and the polymerase lacks strand displacement activity and lacks 5' to 3' exonuclease activity and the ligation reactants encompass a ligase. In some embodiments the ligase is a thermostable ligase. In other embodiments the thermostable ligase is Taq DNA ligase. The reaction mixture is then subjected to a contemporaneous amplification and ligation reaction after which the reaction mixture is subjected to a separation process and thereby distinguishing the amplified target sequence, if any. In some embodiments a method is disclosed wherein a sample, a first primer, a second primer and a prolongation template are combined along with amplification and ligation reactants to form a reaction mixture, wherein the reaction mixture encompasses one, two or three of the following nucleosides adenosine triphosphate, cytidine triphosphate, guanosine triphosphate and thymidine triphosphate but not all four. The reaction mixture is then subjected to a contemporaneous amplification and ligation reaction after which the reaction mixture is subjected to a separation process and thereby distinguishing the amplified target sequence, if any. In some embodiments, the method encompasses DNA in the reaction mixture. In some embodiments the first, the second or the first and the second primers are synthetic. In some embodiments the separation process is electrophoresis. In other embodiments electrophoresis is capillary electrophoresis. In some embodiments the amplified target sequence is an STR locus. In other embodiments, the target sequence is an STR locus wherein the STR locus is any one of CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

Because the amount of sample or DNA present in forensic case can be limited, multiplex PCR is applied. By using multiplex PCR, multiple targets can be amplified simultaneously, for instance multiple STR loci. Using multiplex PCR more information can be generated with limited amounts of sample or DNA.

Accordingly, in some embodiments a method is disclosed wherein a sample, a first primer, a second primer and a prolongation template are combined along with amplification and ligation reactants to form a reaction mixture, wherein the amplification reactants encompass a polymerase and the polymerase lacks strand displacement activity and the ligation reactants encompass a ligase. In some embodiments the amplification reactants encompass a polymerase and the polymerase lacks strand displacement activity and lacks 5' to 3' exonuclease activity and the ligation reactants encompass a ligase. In some embodiments the ligase is a thermostable ligase. In other embodiments the thermostable ligase is Taq DNA ligase. The reaction mixture is then subjected to a contemporaneous amplification and ligation reaction after which the reaction mixture is subjected to a separation process and thereby distinguishing more than one amplified target sequence, if any. In other embodiments, the first, the second or the first and second primers are synthetic primers. In some embodiments the separation process is electrophoresis. In other embodiments electrophoresis is capillary electrophoresis. In some embodiments all of the amplified target sequences are STR loci. In some embodiments not all of the amplified target sequences are STR loci. In some embodiments at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 STR loci are amplified. In some embodiments, not more than 100, not more than 90, not more than 80, not more than 70, not more than 60, not more than 50, not more than 40, not more than 30, not more than 29, not more than 28, not more than 27, not more than 26, not more than 25, not more than 24 STR loci are amplified. In some embodiments, one or more short nucleotide polymorphism is amplified with more than one STR locus. In other embodiments, more than STR locus is selected from the following STR loci CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than a primer that is its reverse complement. In some embodiments the prolongation template is labeled with an affinity label. In other embodiments the affinity label is biotin. In some embodiments the prolongation template is labeled with an affinity label but the first primer and the second primer are not. In some embodiments the prolongation template is labeled with biotin but the first primer and the second primer are not. In some embodiments, the prolongation template is labeled with an affinity label and one of the primers is labeled with an affinity label. In some embodiments, the prolongation template is labeled with biotin and one of the primers is labeled with biotin. In other embodiments, the prolongation template is labeled with an affinity label and each of the primers is labeled with an affinity label. In some embodiments, the prolongation template is labeled with biotin and each of the primers is labeled with biotin. In some embodiments, the prolongation template is not labeled with an affinity label. In other embodiments, the prolongation template is not labeled with biotin. In some embodiments, the first primer is not labeled with an affinity label and the second primer is labeled with an affinity label. In some embodiments, the first primer is not labeled with a biotin and the second primer is labeled with a biotin. In other embodiments, the first primer is labeled with an affinity label and the second primer is detectably labeled. In some embodiments, the first primer is labeled with biotin and the second primer is detectably labeled. In other embodiments, the first primer is labeled with an affinity label and the second primer is detectably labeled, wherein the detectable label is a fluorescent dye. In some embodiments, the first primer is labeled with an affinity label, wherein the affinity label is biotin or streptavidin and the second primer is detectably labeled, wherein the detectable label is a fluorescent dye. In other embodiments, the first primer is labeled with an affinity label, wherein the affinity label is magnetically attractable and the second primer is detectably labeled, wherein the detectable label is a fluorescent dye.

Allelic Ladder

In the instant disclosure provides for an allelic ladder. "Allelic ladder" refers to a nucleic acid size standard that provides size standards for one or more alleles for a particular STR marker. The allelic ladder serves as a reference standard and nucleic acid size marker for the amplified alleles from the STR locus. In some embodiments, the allelic ladder can comprise size standards for the alleles of different STRs. In some embodiments, the allelic ladder can be made of DNA. In some embodiments the allelic ladder can be made of non-naturally occurring nucleic acid analogs. The different individual size standards within an allelic ladder can, in some embodiments can be labeled with a detectable label, e.g., a fluorophore. In some embodiments, the allelic ladder components are labeled with the same fluorophore. In some embodiments, the allelic ladder components are labeled with the different fluorophores. The size standards can be selected to work for a specific pair (or pairs) of oligonucleotides primers. For example if a first set of primers for marker X produces a 150 base pair amplicon corresponding to allele 7, the corresponding marker will serve as a size standard for the 150 base amplicons; while a second pair of primers marker X produces a 175 base pair amplicon corresponding to allele 7, the corresponding marker will serve as a size standard for the 175 base amplicons. Thus different size standards for different size amplicons of the same allele are contemplated. The size standard for a given amplicon derived from a given allele may have nucleic acid base sequence that is the same or different than the nucleic acid base sequence of the amplicon or allele from which the amplicon is derived. For allele analysis in electrophoresis systems the size standard can be selected so as to have the same electrophoretic mobility as the amplicon of interest. Alternatively, in some embodiments, the size standard can be selected so as to have the different electrophoretic mobility than the amplicon of interest, given an understanding of the predicable nature of the difference, the identity of the amplicons could be determined. For allele analysis in mass spectroscopy systems the size standard (weight/charge ratio, not electrophoretic mobility) can be selected so as to have the same signal as the amplicon of interest. Alternatively, in some embodiments, the size standard (weight/charge ratio, not electrophoretic mobility) can be selected so as to have the different separation properties than the amplicon of interest, given an understanding of the predicable nature of the difference, the identity of the amplicons could be determined.

Accordingly, in some embodiments an allelic ladder is disclosed wherein one or more components of the allelic ladder encompasses an allele of an STR locus combined with a prolongation template wherein the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments, at least one component the allelic ladder is an allele of anyone of the STR loci CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043 combined with a prolongation template wherein the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments, at least one component of the allelic ladder is labeled with a detectable label. In some embodiments, the detectable label is a fluorescent dye. In other embodiments, at least one component of the allelic ladder is labeled with an affinity label. In some embodiments, the allelic ladder encompasses a least one allele from more than one, more than two, more than three, more than four, more than five, more than six, more than seven, more than eight, more than nine, more than 10, more than 11, more than 12, more than 13, more than 14, more than 15, more than 16, more than 17, more than 18, more than 19, more than 20, more than 21, more than 22, more than 23, more than 24 STR loci combined with a prolongation template wherein the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments, the allelic ladder encompasses a least one allele from more than one, more than two, more than three, more than four, more than five, more than six, more than seven, more than eight, more than nine, more than 10, more than 11, more than 12, more than 13, more than 14, more than 15, more than 16, more than 17, more than 18, more than 19, more than 20, more than 21, more than 22, more than 23, more than 24 STR loci combined with a prolongation template wherein the prolongation template encompasses a sequence that is the reverse complement of a sequence flanking the target sequence, the complementary prolongation template region, and a sequence that is not complementary to a sequence flanking the target sequence, the non-complementary prolongation template region but encompasses one or more alleles from no more than 50, no more than 40, no more than 30, no more than 29, no more than 28, no more than 27, no more than 26, no more than 25 or no more than 24 STR loci.

In some embodiments, the allelic ladder encompasses an allele of an STR locus, the allele of the STR locus is combined covalently with a prolongation template sequence, the prolongation template sequence encompasses a sequence that is the reverse complement to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides within 100 nucleotides of the STR locus and a sequence that is not the reverse complement to a sequence of 8, 9, 10, 11, 12, 13, 14, 15, 16, 17, 18, 19, 20, 21, 22, 23, 24, 25, 26 or more nucleotides within 100 nucleotides of the STR locus. In other embodiments, the prolongation template sequence encompasses a sequence that is the reverse complement to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides within 100 nucleotides of the STR locus and a sequence that is not the reverse complement to a sequence of 8, 9, 10, 11, 12, 13, 14, 15, 16, 17, 18, 19, 20, 21, 22, 23, 24, 25, 26 or more nucleotides within 200, 300, 400, 500, 600, 700, 800, 900 or 1000 nucleotides of the STR locus A Kit Disclosed herein are kits. "Kit" refers generally to a set of articles or implements which can be used in conjunction with one another to achieve a specific purpose.

In some embodiments, the kit encompasses a first primer, a second primer and a prolongation template, wherein the first primer and the prolongation template possess sequence that is the reverse complement of sequence flanking an STR locus and the second primer is the reverse complement of sequence present in the prolongation template. In other embodiments, the kit also encompasses a container with a polymerase, a container with a ligase, a container with a first primer, a second primer and a prolongation template and a container with a buffer, wherein the first primer and the prolongation template possess sequence that is the reverse complement of sequence flanking an STR locus and the second primer is the reverse complement of sequence present in the prolongation template. While in other embodiments, the kit encompasses a container with an allelic ladder, a polymerase, a container with a ligase, a container with a first primer, a second primer and a prolongation template and a container with a buffer. In some embodiments the prolongation template is the reverse complement of a sequence flanking the target sequence over its entire length. In other embodiments the prolongation template encompasses a sequence that is the reverse complement of a sequence flanking the target sequence, the complementary prolongation template region, and a sequence that is not complementary to a sequence flanking the target sequence, the non-complementary prolongation template region. In some embodiments the non-complementary prolongation template region sequence is longer in nucleotides than the second primer that is its reverse complement.

The primers can be maintained in the same container or in separate, individual containers. In some embodiments, the primers and the prolongation template are in the same container. In other embodiments, one or more primers and the prolongation template are in separate containers. In some embodiments, the first the second or the first and the second primers are detectably labeled. In other embodiments, the prolongation template is detectably labeled. In some embodiments, the first the second or the first and the second primers are detectably labeled. In other embodiments, the prolongation template is detectably labeled. In some embodiments, the first the second or the first or the second primers are affinity labeled. In other embodiments, the prolongation template is affinity labeled. In some embodiments, the first primer is affinity labeled and the second primer is detectably labeled.

EXAMPLES

Integrated Single Tube Extension Ligation with Single Prolongation Template

A simultaneous multiplex PCR ligation reaction is used to amplify and combine the CODIS STR loci with specific prolongation templates. 1 ng. of genomic DNA isolated from the 9947A cell line is used for target amplification. The reaction is performed in a reaction volume of 50 µl. using a master mix containing 1× Phusion HF buffer (Thermo Scientific), Phusion Hot Start II High-Fidelity DNA polymerase (Thermo Scientific), 0.1 µg/µl Tma DNA ligase, 0.2 mM each deoxynucleotide triphosphate, 2.0 mM MgCl$_2$ and 0.5 mM NAD$^+$. Representative reaction conditions are: 98° C. for 30 s; 28 cycles at 98° C. for 10 s, 55° C. for 30 s, 72° C. for 15 s; 72° C. for 5 min; and then 4° C. soak. The final products are subjected to capillary electrophoresis.

Each sample for analysis is prepared by adding 1 µl. of the final reaction product to of Hi-Di formamide (Applied Biosystems) containing 0.75 µl. of GS500ROX size standard (Applied Biosystems). Samples are placed immediately into the instrument for analysis without heat denaturation or snap cooling. Samples are injected for 5 s at 15 kV and separated at 15 kV for 24 min with a run temperature of 60° C. Standard electrophoretic conditions are used including buffer and polymer.

Integrated Single Tube Extension Ligation with Two Prolongation Templates

A simultaneous multiplex PCR ligation reaction is used to amplify and combine the COD'S STR loci with specific prolongation templates. 1 ng. of genomic DNA isolated from the 9947A cell line is used for target amplification. The reaction is performed in a reaction volume of 50 using a master mix containing 1× Phusion HF buffer (Thermo Scientific), Phusion Hot Start II High-Fidelity DNA polymerase (Thermo Scientific), 0.1 WA Tma DNA ligase, 0.2 mM each deoxynucleotide triphosphate, 2.0 mM MgCl$_2$ and 0.5 mM NAD$^+$. Representative reaction conditions are: 98° C. for 30 s; 28 cycles at 98° C. for 10 s, 55° C. for 30 s, 72° C. for 15 s; 72° C. for 5 min; and then 4° C. soak. The final products are subjected to capillary electrophoresis.

Each sample for analysis is prepared by adding 1 µl. of the final reaction product to 194 of Hi-Di formamide (Applied Biosystems) containing 0.75 µl. of GS500ROX size standard (Applied Biosystems). Samples are placed immediately into the instrument for analysis without heat denaturation or snap cooling. Samples are injected for 5 s at 15 kV and separated at 15 kV for 24 min with a run temperature of 60° C. Standard electrophoretic conditions are used including buffer and polymer.

I claim:

1. A method comprising:
   a. combining DNA, a DNA ligase, a DNA polymerase, ATP, CTP, GTP, TTP, a first primer, a second primer and a prolongation template in a reaction vessel, the first primer and the prolongation template are the reverse complement of a same chromosomal strand, the first primer flanking one side of a short tandem repeat (STR) locus and the prolongation template flanking the other side of the STR locus, the second primer is the reverse complement to the prolongation template over the length of the second primer;
   b. performing a DNA polymerase mediated extension and a DNA ligation reaction and forming a reaction product; and
   c. subjecting the reaction product and an allelic ladder to capillary electrophoresis and thereby resolving the reaction product, wherein the allelic ladder comprises two or more alleles of the STR locus, each allele of the STR locus is combined with the prolongation template comprising a sequence that is the reverse complement to a sequence of at least contiguous 10 nucleotides within 100 contiguous nucleotides of the STR locus and a sequence that is not the reverse complement to a sequence of 10 or more contiguous nucleotides within 100 contiguous nucleotides of the STR locus.

2. The method of claim 1, wherein the prolongation template is from 20-1000 nucleotides in length.

3. The method of claim 1, wherein the first primer is affinity labeled.

4. The method of claim 1, wherein the second primer is detectably labeled.

5. The method of claim 1, wherein the STR locus is selected from CSF1PO, FGA, TH01, TPDX, vWA, D3S1358, D5S818, D7S820, D8S1179, D13S317, D16S539, D18S51, D21S11, D2S1338, D19S433, D12S391, D1S1656, D2S441, D10S1248, D22S1045, SE33, Penta D, Penta E and D6S1043.

6. The method of claim 1, wherein the second primer is from 20-50 nucleotides in length.

7. The method of claim 1, wherein the sequence of the first primer comprises SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO.:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, or SEQ ID NO:68.

* * * * *

```
SEQUENCE LISTING

<160> NUMBER OF SEQ ID NOS: 70

<210> SEQ ID NO 1
<211> LENGTH: 21
<212> TYPE: DNA
<213> ORGANISM: Artificial Sequence
<220> FEATURE:
<223> OTHER INFORMATION: synthesized

<400> SEQUENCE: 1
atcatcatca tcatcatcat c                                             21

<210> SEQ ID NO 2
<211> LENGTH: 20
<212> TYPE: DNA
<213> ORGANISM: Artificial Sequence
<220> FEATURE:
<223> OTHER INFORMATION: synthesized

<400> SEQUENCE: 2
gatagataga tagatagata                                               20

<210> SEQ ID NO 3
<211> LENGTH: 15
<212> TYPE: DNA
<213> ORGANISM: Artificial Sequence
<220> FEATURE:
<223> OTHER INFORMATION: synthesized

<400> SEQUENCE: 3
attgcattgc attgc                                                    15
```

-continued

```
<210> SEQ ID NO 4
<211> LENGTH: 20
<212> TYPE: DNA
<213> ORGANISM: Artificial Sequence
<220> FEATURE:
<223> OTHER INFORMATION: synthesized

<400> SEQUENCE: 4
atcgatcgaa cgatcgatcg                                            20

<210> SEQ ID NO 5
<211> LENGTH: 15
<212> TYPE: DNA
<213> ORGANISM: Artificial Sequence
<220> FEATURE:
<223> OTHER INFORMATION: synthesized

<400> SEQUENCE: 5
aatgaatgaa tgatg                                                 15

<210> SEQ ID NO 6
<211> LENGTH: 28
<212> TYPE: DNA
<213> ORGANISM: Artificial Sequence
<220> FEATURE:
<223> OTHER INFORMATION: synthesized

<400> SEQUENCE: 6
atccatcgat ccatcgatcg atccatcc                                   28

<210> SEQ ID NO 7
<211> LENGTH: 23
<212> TYPE: DNA
<213> ORGANISM: Homo sapiens

<400> SEQUENCE: 7
acagtaactg ccttcataga tag                                        23

<210> SEQ ID NO 8
<211> LENGTH: 22
<212> TYPE: DNA
<213> ORGANISM: Homo sapiens

<400> SEQUENCE: 8
tacttagaac agggtctgac ac                                         22

<210> SEQ ID NO 9
<211> LENGTH: 22
<212> TYPE: DNA
<213> ORGANISM: Homo sapiens

<400> SEQUENCE: 9
gtgtcagacc ctgttctaag ta                                         22

<210> SEQ ID NO 10
<211> LENGTH: 22
<212> TYPE: DNA
<213> ORGANISM: Homo sapiens

<400> SEQUENCE: 10
ctatctatga aggcagttac tg                                         22

<210> SEQ ID NO 11
<211> LENGTH: 26
<212> TYPE: DNA
```

<213> ORGANISM: Homo sapiens

<400> SEQUENCE: 11
aaataaaatt aggcatattt acaagc					26

<210> SEQ ID NO 12
<211> LENGTH: 22
<212> TYPE: DNA
<213> ORGANISM: Homo sapiens

<400> SEQUENCE: 12
caattacaga caatcactca gc					22

<210> SEQ ID NO 13
<211> LENGTH: 23
<212> TYPE: DNA
<213> ORGANISM: Homo sapiens

<400> SEQUENCE: 13
gctgagtgat ttgtctgtaa ttg					23

<210> SEQ ID NO 14
<211> LENGTH: 26
<212> TYPE: DNA
<213> ORGANISM: Homo sapiens

<400> SEQUENCE: 14
gcttgtaaat atgcctaatt ttattt					26

<210> SEQ ID NO 15
<211> LENGTH: 21
<212> TYPE: DNA
<213> ORGANISM: Homo sapiens

<400> SEQUENCE: 15
cctgttcctc ccttatttcc c					21

<210> SEQ ID NO 16
<211> LENGTH: 21
<212> TYPE: DNA
<213> ORGANISM: Homo sapiens

<400> SEQUENCE: 16
caccatggag tctgtgttcc c					21

<210> SEQ ID NO 17
<211> LENGTH: 21
<212> TYPE: DNA
<213> ORGANISM: Homo sapiens

<400> SEQUENCE: 17
gggaacacag actccatggt g					21

<210> SEQ ID NO 18
<211> LENGTH: 21
<212> TYPE: DNA
<213> ORGANISM: Homo sapiens

<400> SEQUENCE: 18
gggaaataag ggaggaacag g					21

<210> SEQ ID NO 19
<211> LENGTH: 22

<212> TYPE: DNA
<213> ORGANISM: Homo sapiens

<400> SEQUENCE: 19
cttagggaac cctcactgaa tg                                              22

<210> SEQ ID NO 20
<211> LENGTH: 22
<212> TYPE: DNA
<213> ORGANISM: Homo sapiens

<400> SEQUENCE: 20
gcaaataaac gctgacaagg ac                                              22

<210> SEQ ID NO 21
<211> LENGTH: 22
<212> TYPE: DNA
<213> ORGANISM: Homo sapiens

<400> SEQUENCE: 21
gtccttgtca gcgtttattt gc                                              22

<210> SEQ ID NO 22
<211> LENGTH: 22
<212> TYPE: DNA
<213> ORGANISM: Homo sapiens

<400> SEQUENCE: 22
cattcagtga gggttcccta ag                                              22

<210> SEQ ID NO 23
<211> LENGTH: 26
<212> TYPE: DNA
<213> ORGANISM: Homo sapiens

<400> SEQUENCE: 23
aataatcagt atgtgacttg gattga                                          26

<210> SEQ ID NO 24
<211> LENGTH: 22
<212> TYPE: DNA
<213> ORGANISM: Homo sapiens

<400> SEQUENCE: 24
tccatctatc catccatcct at                                              22

<210> SEQ ID NO 25
<211> LENGTH: 22
<212> TYPE: DNA
<213> ORGANISM: Homo sapiens

<400> SEQUENCE: 25
ataggatgga tggatagatg ga                                              22

<210> SEQ ID NO 26
<211> LENGTH: 26
<212> TYPE: DNA
<213> ORGANISM: Homo sapiens

<400> SEQUENCE: 26
tcaatccaag tcacatactc attatt                                          26

<210> SEQ ID NO 27

```
<211> LENGTH: 21
<212> TYPE: DNA
<213> ORGANISM: Homo sapiens

<400> SEQUENCE: 27
cagagcaaga ccctgtctca t                                              21

<210> SEQ ID NO 28
<211> LENGTH: 21
<212> TYPE: DNA
<213> ORGANISM: Homo sapiens

<400> SEQUENCE: 28
atacatgcaa gcctctgttg a                                              21

<210> SEQ ID NO 29
<211> LENGTH: 21
<212> TYPE: DNA
<213> ORGANISM: Homo sapiens

<400> SEQUENCE: 29
tcaacagagg cttgcatgta t                                              21

<210> SEQ ID NO 30
<211> LENGTH: 21
<212> TYPE: DNA
<213> ORGANISM: Homo sapiens

<400> SEQUENCE: 30
atgagacagg gtcttgctct g                                              21

<210> SEQ ID NO 31
<211> LENGTH: 20
<212> TYPE: DNA
<213> ORGANISM: Homo sapiens

<400> SEQUENCE: 31
gggtgatttt cctctttggt                                                20

<210> SEQ ID NO 32
<211> LENGTH: 33
<212> TYPE: DNA
<213> ORGANISM: Homo sapiens

<400> SEQUENCE: 32
ataaataagg atacagataa agatacaaat gtt                                 33

<210> SEQ ID NO 33
<211> LENGTH: 33
<212> TYPE: DNA
<213> ORGANISM: Homo sapiens

<400> SEQUENCE: 33
aacatttgta tctttatctg tatccttatt tat                                 33

<210> SEQ ID NO 34
<211> LENGTH: 20
<212> TYPE: DNA
<213> ORGANISM: Homo sapiens

<400> SEQUENCE: 34
accaaagagg aaaatcaccc                                                20
```

```
<210> SEQ ID NO 35
<211> LENGTH: 27
<212> TYPE: DNA
<213> ORGANISM: Homo sapiens

<400> SEQUENCE: 35
gaacacttgt catagtttag aacgaac                                              27

<210> SEQ ID NO 36
<211> LENGTH: 20
<212> TYPE: DNA
<213> ORGANISM: Homo sapiens

<400> SEQUENCE: 36
tcattgacag aattgcacca                                                      20

<210> SEQ ID NO 37
<211> LENGTH: 20
<212> TYPE: DNA
<213> ORGANISM: Homo sapiens

<400> SEQUENCE: 37
tcattgacag aattgcacca                                                      20

<210> SEQ ID NO 38
<211> LENGTH: 20
<212> TYPE: DNA
<213> ORGANISM: Homo sapiens

<400> SEQUENCE: 38
tggtgcaatt ctgtcaatga                                                      20

<210> SEQ ID NO 39
<211> LENGTH: 27
<212> TYPE: DNA
<213> ORGANISM: Homo sapiens

<400> SEQUENCE: 39
tttgtatttc atgtgtacat tcgtatc                                              27

<210> SEQ ID NO 40
<211> LENGTH: 28
<212> TYPE: DNA
<213> ORGANISM: Homo sapiens

<400> SEQUENCE: 40
cacagtgaaa ataatctaca ggataggt                                             28

<210> SEQ ID NO 41
<211> LENGTH: 28
<212> TYPE: DNA
<213> ORGANISM: Homo sapiens

<400> SEQUENCE: 41
acctatcctg tagattattt tcactgtg                                             28

<210> SEQ ID NO 42
<211> LENGTH: 27
<212> TYPE: DNA
<213> ORGANISM: Homo sapiens

<400> SEQUENCE: 42
gatacgaatg tacacatgaa atacaaa                                              27
```

```
<210> SEQ ID NO 43
<211> LENGTH: 20
<212> TYPE: DNA
<213> ORGANISM: Homo sapiens

<400> SEQUENCE: 43
tctgacccat ctaacgccta                                          20

<210> SEQ ID NO 44
<211> LENGTH: 27
<212> TYPE: DNA
<213> ORGANISM: Homo sapiens

<400> SEQUENCE: 44
tcaatcatct atctatcttt ctgtctg                                  27

<210> SEQ ID NO 45
<211> LENGTH: 27
<212> TYPE: DNA
<213> ORGANISM: Homo sapiens

<400> SEQUENCE: 45
cagacagaaa gatagataga tgattga                                  27

<210> SEQ ID NO 46
<211> LENGTH: 20
<212> TYPE: DNA
<213> ORGANISM: Homo sapiens

<400> SEQUENCE: 46
taggcgttag atgggtcaga                                          20

<210> SEQ ID NO 47
<211> LENGTH: 21
<212> TYPE: DNA
<213> ORGANISM: Homo sapiens

<400> SEQUENCE: 47
atacagacag acagacaggt g                                        21

<210> SEQ ID NO 48
<211> LENGTH: 23
<212> TYPE: DNA
<213> ORGANISM: Homo sapiens

<400> SEQUENCE: 48
agagatggat gatagataca tgc                                      23

<210> SEQ ID NO 49
<211> LENGTH: 23
<212> TYPE: DNA
<213> ORGANISM: Homo sapiens

<400> SEQUENCE: 49
gcatgtatct atcatccatc tct                                      23

<210> SEQ ID NO 50
<211> LENGTH: 21
<212> TYPE: DNA
<213> ORGANISM: Homo sapiens

<400> SEQUENCE: 50
cacctgtctg tctgtctgta t                                        21
```

<210> SEQ ID NO 51
<211> LENGTH: 21
<212> TYPE: DNA
<213> ORGANISM: Homo sapiens

<400> SEQUENCE: 51
tgagtgacaa attgagacct t                                      21

<210> SEQ ID NO 52
<211> LENGTH: 26
<212> TYPE: DNA
<213> ORGANISM: Homo sapiens

<400> SEQUENCE: 52
aatagtagca actgttattg taagac                                 26

<210> SEQ ID NO 53
<211> LENGTH: 26
<212> TYPE: DNA
<213> ORGANISM: Homo sapiens

<400> SEQUENCE: 53
gtcttacaat aacagttgct actatt                                 26

<210> SEQ ID NO 54
<211> LENGTH: 21
<212> TYPE: DNA
<213> ORGANISM: Homo sapiens

<400> SEQUENCE: 54
aaggtctcaa tttgtcactc a                                      21

<210> SEQ ID NO 55
<211> LENGTH: 18
<212> TYPE: DNA
<213> ORGANISM: Homo sapiens

<400> SEQUENCE: 55
attccccaag tgaattgc                                          18

<210> SEQ ID NO 56
<211> LENGTH: 26
<212> TYPE: DNA
<213> ORGANISM: Homo sapiens

<400> SEQUENCE: 56
tcgtctatct atccagtcta tctacc                                 26

<210> SEQ ID NO 57
<211> LENGTH: 26
<212> TYPE: DNA
<213> ORGANISM: Homo sapiens

<400> SEQUENCE: 57
ggtagataga ctggatagat agacga                                 26

<210> SEQ ID NO 58
<211> LENGTH: 18
<212> TYPE: DNA
<213> ORGANISM: Homo sapiens

<400> SEQUENCE: 58

```
gcaattcact tggggaat                                               18

<210> SEQ ID NO 59
<211> LENGTH: 22
<212> TYPE: DNA
<213> ORGANISM: Homo sapiens

<400> SEQUENCE: 59
gagcaagaca ccatctcaag aa                                          22

<210> SEQ ID NO 60
<211> LENGTH: 30
<212> TYPE: DNA
<213> ORGANISM: Homo sapiens

<400> SEQUENCE: 60
agagaatcat aaacataaat gtaaaatttc                                  30

<210> SEQ ID NO 61
<211> LENGTH: 30
<212> TYPE: DNA
<213> ORGANISM: Homo sapiens

<400> SEQUENCE: 61
gaaattttac atttatgttt atgattctct                                  30

<210> SEQ ID NO 62
<211> LENGTH: 22
<212> TYPE: DNA
<213> ORGANISM: Homo sapiens

<400> SEQUENCE: 62
ttcttgagat ggtgtcttgc tc                                          22

<210> SEQ ID NO 63
<211> LENGTH: 18
<212> TYPE: DNA
<213> ORGANISM: Homo sapiens

<400> SEQUENCE: 63
ggcgactgag caagactc                                               18

<210> SEQ ID NO 64
<211> LENGTH: 27
<212> TYPE: DNA
<213> ORGANISM: Homo sapiens

<400> SEQUENCE: 64
tgtaaggagt tttctcaatt aataacc                                     27

<210> SEQ ID NO 65
<211> LENGTH: 27
<212> TYPE: DNA
<213> ORGANISM: Homo sapiens

<400> SEQUENCE: 65
ggttattaat tgagaaaact ccttaca                                     27

<210> SEQ ID NO 66
<211> LENGTH: 18
<212> TYPE: DNA
<213> ORGANISM: Homo sapiens

<400> SEQUENCE: 66
```

```
gagtcttgct cagtcgcc                                                 18

<210> SEQ ID NO 67
<211> LENGTH: 20
<212> TYPE: DNA
<213> ORGANISM: Homo sapiens

<400> SEQUENCE: 67
tggaaacaga aatggcttgg                                               20

<210> SEQ ID NO 68
<211> LENGTH: 20
<212> TYPE: DNA
<213> ORGANISM: Homo sapiens

<400> SEQUENCE: 68
cttccttccc tcctgcaatc                                               20

<210> SEQ ID NO 69
<211> LENGTH: 20
<212> TYPE: DNA
<213> ORGANISM: Homo sapiens

<400> SEQUENCE: 69
gattgcagga gggaaggaag                                               20

<210> SEQ ID NO 70
<211> LENGTH: 20
<212> TYPE: DNA
<213> ORGANISM: Homo sapiens

<400> SEQUENCE: 70
ccaagccatt tctgtttcca                                               20
```